United States Patent [19]

Fu et al.

[11] Patent Number: 5,464,627
[45] Date of Patent: Nov. 7, 1995

[54] EXTRUDIBLE WET PASTE COMPOSITION OF AN AGRICULTURALLY ACTIVE CHEMICAL; FREE-FLOWING, WATER-DISPERSIBLE OR WATER-SOLUBLE GRANULES THEREFROM

[75] Inventors: Edward Fu, Newark, Del.; Kolazi S. Narayanan, Palisades Park, N.J.

[73] Assignee: ISP Investments Inc., Wilmington, Del.

[21] Appl. No.: 149,869

[22] Filed: Nov. 10, 1993

[51] Int. Cl.⁶ ................................................. A01N 25/14
[52] U.S. Cl. .......................................... 424/409; 424/405
[58] Field of Search ................................. 424/405, 407, 424/409, 489, 501; 524/104

[56] References Cited

U.S. PATENT DOCUMENTS

| | | | |
|---|---|---|---|
| 3,943,253 | 3/1976 | Barer et al. ........................... | 514/558 |
| 4,277,582 | 7/1981 | Mueller et al. ........................ | 525/421 |
| 4,962,133 | 10/1990 | Chromecek et al. ................. | 521/56 |
| 5,180,587 | 1/1993 | Moore .................................... | 424/408 |
| 5,232,701 | 8/1993 | Ogawa et al. ......................... | 424/408 |

FOREIGN PATENT DOCUMENTS

| | | |
|---|---|---|
| 0415568 | 3/1991 | European Pat. Off. . |
| 8800184 | 1/1988 | WIPO . |

*Primary Examiner*—Thurman K. Page
*Assistant Examiner*—Neil Levy
*Attorney, Agent, or Firm*—Walter Katz; Marilyn J. Maue; Joshua J. Ward

[57] ABSTRACT

An extrudible, wet paste composition of an agriculturally active chemical is provided herein which is used for forming water-dispersible or water-soluble granules thereof. These granules form stable suspensions or solutions in water which provide efficient delivery systems for such agricultural chemicals.

4 Claims, No Drawings

EXTRUDIBLE WET PASTE COMPOSITION OF AN AGRICULTURALLY ACTIVE CHEMICAL; FREE-FLOWING, WATER-DISPERSIBLE OR WATER-SOLUBLE GRANULES THEREFROM

BACKGROUND OF THE INVENTION

1. Field of the Invention

This invention relates to delivery systems for agriculturally active chemicals, and, more particularly, to extrudible wet paste compositions which are useful for forming free-flowing, water-dispersible or water-soluble granules of such agricultural chemicals.

2. Description of the Prior Art

Water-dispersible or water-soluble granules are important delivery vehicles for agriculturally active chemicals because they can be transported more economically than suspension concentrates or aqueous solutions of such chemicals. However, such granules must be free-flowing, have excellent friability resistance, and form stable suspensions or aqueous solutions when dispersed or dissolved in water. Preferably, such granules should be capable of manufacture by extrusion from a wet paste composition of the chemical, followed by drying. In addition, the granule form of the chemical should enhance or not reduce the efficacy of the chemical upon delivery to the desired plant site.

Accordingly, it is an object of this invention to provide a wet paste composition of an agriculturally active chemical which is extrudible into free-flowing granules which can be dispersed or dissolved rapidly in water as a stable suspension or solution.

Another object is to provide such granule delivery systems for agriculturally active-chemicals which have excellent friability resistance.

Still another object herein is to provide such granules which enhance or do not reduce the efficacy of the agricultural chemical upon application to a plant site.

SUMMARY OF THE INVENTION

What is provided herein is a wet paste composition of an agriculturally active chemical which includes a water-insoluble, film-forming polymer. The composition is used for forming free-flowing granules of such chemical which can disperse or dissolve rapidly in water. The granule material exhibits excellent friability resistance, and, in use, actually enhances the efficacy of the agricultural chemical by forming a film of the polymer on the plant surface which is rainfast.

DETAILED DESCRIPTION OF THE INVENTION

Wet Paste Composition

1. Essential Components

The wet paste composition of the invention comprises:

(a) An agriculturally active chemical which is defined as compounds and mixtures thereof which can be used as agricultural fertilizers, nutrients, plant growth accelerants, herbicides, plant growth controlling chemicals, and chemicals which are effective in killing plants, insects, microorganisms, fungi, bacteria and the like which are commonly referred to as insecticides, bactericides, fungicides, nematocides, fumigants, synergists. Typical of such chemicals are water soluble herbicides such as phosphonomethyl glycine, and 2,4-dichlorophenoxy acetic acid; and water insoluble fungicides such as tetrachloroisophthalonitrile (chlorothalonil).

(b) A water-insoluble, film-forming polymer which adheres to the plant surfaces and resists wash-off of the agricultural chemical by rain, thus extending the contact time of the chemical on the site resulting in an enhanced effectiveness of the chemical. Typical of such polymers are copolymers of N-vinylpyrrolidone with α-olefins, vinyl acetate, styrene acrylates, acrylic acids, amides, copolymers of vinyl ether and maleic acid, maleic acid, mono and diesters of maleic acids, and the like. Preferred are graft polymers of vinylpyrrolidone and α-olefins having from 4 to 30 carbon atoms, and the vinylpyrrolidone content is 10–90%.

Polymers particularly suitable for use in the present invention include polymers, such as, Ganex® 516, which is copolymer of an α-olefin and N-vinylpyrrolidone (50/50 percent mixture). Typically, such α-olefins contain up to 20 carbon atoms and preferably, contain 16. The weight average molecular weight of such polymers is generally greater than about 20,000. Particularly suitable are water-insoluble polymers, such as, Agrimer™ AL 25 (International Specialty Products (ISP), which is a copolymer of an α-olefin having the formula $C_{14}H_{29}CH{=}CH_2$ (50%) and N-vinylpyrrolidone (50%), and Agrimer™ AL 30 (ISP), which is a copolymer of an α-olefin having 20 carbon atoms (80%), and N-vinylpyrrolidone (20%). All percents herein are percent by weight based on the total weight of the composition.

(c) An anionic surfactant such as phosphate esters and their salts, alkyl sulfates, sulfonates, and their salts, salts of sulfate nonylphenoxypoly(ethyleneoxy) ethanol, salts of alkylbenzene sulfonates, salts of alkylnaphthalene sulfonates, and sulfonated aliphatic polyesters and their salts. (See, for example, McCutcheon's, *Emulsifiers and Detergents* (1989), published by McCutcheon's Division of M.C. Publishing Co., Glen Rock, N.J.)

(d) An N-alkylpyrrolidone with at least one long chain alkylpyrrolidone such as a $C_6$–$C_{24}$ alkylpyrrolidone, and mixtures thereof. Such compounds includes N-octylpyrrolidone.

(e) Water is another essential component of the wet paste composition of the invention. The presence of water therein acts to dissolve the anionic surfactant, and, in a predetermined amount, it provides adequate cohesion for the free-flowing granules without causing them to stick together. If necessary, water may be added to the composition if the water content of commercial Agrimax™ is insufficient to dissolve the anionic surfactant component.

Components (b) through (e) are present in commercial product Agrimax™ adjuvant formulations (International Specialty Products).

2. Optional Components (a) A small chain ($C_1$–$C_4$) alkylpyrrolidone such as N-methylpyrrolidone may be included in an amount effective to help maintain the solubility of the long chain alkylpyrrolidone component.

(b) A disintegrant such as a crosslinked polyvinylpyrrolidone may be included to assist in the break-up of the granules.

(c) An inorganic carbonate may be present to form a salt with an agricultural chemical.

(d) A dispersant such as a lignosulfonate or naphthalene sulfonate formaldehyde condensate may be included to disperse the granules.

(e) A wetting agent such as naphthalene sulfonate may be present to solubilize the components.

(f) A defoamer such as soda soap may be included if foaming is a problem.

Preparation of the Wet Paste Composition and Granules

The active and inert ingredients of the wet paste composition of the invention are weighed and placed in a twin shell blender and blended for 10 minutes. For water dispersible granule formulations, the sample was then air milled in a 2 in. Micron-Master® Jet Pulverizer at a feed rate of 20 g/min. and at an air pressure of 100 psi. Agrimax™ adjuvant then was pipetted into the mixing bowl with the solid ingredients, and the resulting wet mass was mixed at speed 2 for 15 minutes, and at speed 3 for another 15 minutes. The sample was then transferred to an LCI Benchtop Granulator, a basket type extruder with adjustable speed and interchangeable screens. Extrusion was carried out at a speed of 10 (maximum) at a screen opening of 1 mm. Other methods such as pan granulation and fluidized bed granulation also may be used in place of extrusion.

After extrusion, the sample was dried in a Retsch TG 1 fluid bed dryer for 30 minutes at 40° C. with maximum air speed. The dried product was cooled at ambient temperature for more than 1 hour, then sieved through a 40 mesh (0.425 mm) screen for 3 minutes on a Meinzer sieve shaker set at 3 (low intensity). The granules obtained from a 40 mesh screen were then evaluated.

The extrudible wet paste composition of the invention for forming free-flowing granules of an agriculturally active chemical, which can be dispersed or dissolved rapidly in water, comprises, by weight:

(a) 20–80%, preferably 50–70%, of an agriculturally active chemical, (b) 1–4%, preferably 1.5–2.5%, of a water-insoluble, film-forming polymer, (c) 0.5–3%, preferably 1–2%, of an anionic surfactant, (d) 2–10%, preferably 5–7.5%, of a $C_6$–$C_{24}$ alkylpyrrolidone, (e) 2–8%, preferably 3–6%, of water, and, optionally, (f) 0–4%, preferably 0–3%, of a $C_1$–$C_4$ alkylpyrrolidone, (g) 0–80%, preferably 0–50%, of a salt former, preferably sodium hydrogen carbonate, (h) 0–4%, preferably 0–3% of a disintegrant, preferably, crosslinked polyvinylpyrrolidone, (i) 0–10%, preferably 0–8%, of a dispersant, (j) 0–8%, preferably 0–5%, of a wetting agent, and (k) 0–2%, preferably 0–1%, of a defoamer.

A free-flowing granule was made by drying the extruded wet paste composition given above. Such free-flowing granules have a Friability Index of >95, a percent solids suspended of 80–90%, a Sedimentation Index of <1 or 0.1 ml sediment/15 granules, and a number of inversions index of less than 100 at 20 inversions/minute.

TABLE 1

| Composition of Agrimax ™ 3 and Agrimax ™ 5 (% by wt.) | | |
|---|---|---|
| | Agrimax ™ 3 | Agrimax ™ 5 |
| Agrimer ™ AL 25* | 15.0 | 20.0 |
| Sodium Dodecylsulfate | 11.4 | 11.0 |
| N-Methylpyrrolidone | — | 16.0 |
| N-Octylpyrrolidone | 45.7 | 16.0 |
| N-Dodecylpyrrolidone | — | 11.0 |
| Water | 27.9 | 26.0 |

*copolymer of vinyl pyrrolidone and $C_{16}$ α-olefin in 50:50 weight ratio with a number average molecular weight of about 9500

| Composition of Glyphosate/Agrimax ™ 3 Granules (% by wt.) | | |
|---|---|---|
| | Suitable | Preferred |
| Glyphosate | 40–60 | 42–48 |
| Sodium bicarbonate (salt former) | 30–50 | 42–48 |
| Water-insoluble polymer | 1–4 | 2–3 |
| Anionic surfactant | 1–3 | 1.5–2 |
| Long chain alkylpyrrolidone | 4–10 | 6–9 |

| Composition of Chlorothalonil/Agrimax ™ 3 Granules (% by wt.) | | |
|---|---|---|
| | Suitable | Preferred |
| Chlorothalonil (technical) | 60–80 | 65–75 |
| Lignosulfonate (dispersant) | 2–8 | 3–5 |
| Napthalene sulfonate formaldehyde condensate (dispersant) | 2–8 | 3–5 |
| Napthalene sulfonate (wetting agent) | 1–3 | 1–1.5 |
| Soda Soap (defoamer) | 0.5–1.5 | 0.7–1 |
| Agrimer ™ XL* or Agrimer ™ AT* (dispersant) | 1–5 | 1.5–3 |
| Water-insoluble polymer | 1–4 | 2–3 |
| Anionic surfactant | 1–3 | 1.5–2 |
| Long chain alkylpyrrolidone | 4–10 | 6–9 |

*crosslinked polyvinylpyrrolidone

Granule Evaluation Tests

Friability—Measurements were carried out on a Vanderkamp® friabilator. 10 g of sample was loaded into a Roche drum, along with 25 PFTE balls of 0.6 cm diameter, which was then attached to the friabilator. The sample was subjected to 400 rotations, where each rotation causes the sample to fall a distance of 15 cm. Afterwards, the sample was sieved through a 40 mesh screen, and the weight of sample remaining above 40 mesh was determined. A friability index was calculated as follows:

$$\text{Friability Index} = \frac{\text{sample wt above 40 mesh}}{\text{total sample wt}} \times 100 \quad (1)$$

Crush Strength—For each sample, at least 15 granules were placed on a balance, and were crushed firmly with a spatula. The force registered at breakage was recorded for each one, and the median of 15 measurements was determined.

Foaming—100 mL of 342 ppm hard water and 5 g of sample were added to a 500 mL fleaker™. The suspension was shaken vigorously by hand 60 times, and then allowed to settle for 2 min. The suspension was again shaken 60 times, after which the foam height was measured after 10 s and 2 min. The last step was repeated to produce a second set of values at 10 s and 2 min. A foaming index was calculated as follows:

$$\text{Foam Index} = \frac{(10 \text{ s ht.} \times 2 \text{ min. ht.})1 + (10 \text{ s ht.} \times 2 \text{ min. ht.})2}{20} \quad (2)$$

Dissolution—50 mL of 342 ppm hard water was added to a 100 mL graduated cylinder. 0.5 g of sample was added and the cylinder was inverted at the rate of 20 inversions per minute. The cylinder was inspected after every five inversions. The test was terminated when complete dissolution was observed, and the number of inversions at that point was recorded.

Cone Dispersion—15 g of sample was dispersed in 800 mL of 342 ppm hard water by stirring with a magnetic stir bar for 2 min. The suspension was poured into a 1 L Imhoff dispersion cone, and allowed to settle for 5 min. The sediment volume was then determined, and a sedimentation index was calculated as follows $$\text{Sed. Index} = \frac{\text{sed. vol. (mL)}}{\text{sample wt. (g)}} \times 100 \quad (3)$$

Filtration Suspension—A quantity of sample containing 1 g of technical was added to 250 mL of 342 ppm hard water in a fleaker™. After 5 min, the fleaker was inverted 30 times to disperse the sample. Immediately, the suspension was then poured into an Imhoff dispersion cone. After 30 min, the upper 90% of the suspension was removed by aspiration. The remaining sample was vacuum filtered through a No. 3 Whatman filter paper, dried, and weighed to determine residual solids. The percent suspended was calculated as follows:

$$\% \text{ Susp.} = \frac{[\text{sample wt} - (\text{residual wt} - 0.1 \times \text{sample wt})]}{\text{sample wt}} \times 100 \quad (4)$$

Greenhouse Biological Tests

Plant Material—Experimental and commercial glyphosate formulations were tested for their efficacy against smooth pigweed (*Amaranthus hybridus*), giant foxtail (*Setaria faberii*), and velvetleaf (*Abutilon theophrasti*). These species represent grasses and broadleaf weeds with different surface properties. The plants were grown in 10 cm pots, kept in a glasshouse and watered on a daily basis. After the seedlings had germinated and grown to a height of 5 cm, they were thinned to give three plants per pot. Tests were carried out when plants were at the 4–6 leaf growth stage. Plant height ranged from approximately 15 cm for velvetleaf to 35 cm for foxtail.

Application Procedures—All applications were made in a track room using a hydraulic three nozzle boom. Nozzle spacing on the boom was set at 51 cm (nozzle center to nozzle center). Spray volume for all tests was 180 L/ha, using TeeJet® XR8003VS nozzles operated at 276 kPa and at a speed of 7.7 km/h. Pressure was supplied as compressed air to a cornelius can containing spray solution. Each of the five replicates were sprayed with a separate pass of the sprayer. Nozzle to target distance was maintained at 45 cm, and the test plants were placed in a line 50 cm apart directly under the center nozzle.

Plant Handling, Storage and Assessments—Once sprayed, the plants were removed from the track room and placed on a bench to dry. Care was taken to prevent treated plants from touching each other. After drying (approximately 30 min.) the plants were removed to a greenhouse where they were set out as randomized complete blocks.

Assessments of phytotoxicity were carried out at intervals up to 14 days after application. Damage was scored on a 0–10 scale, where 0=no effect and 10=dead plants. 14 days after application the biomass of the above-ground plant parts was determined. The plants were weighed again after drying at 75° C. for a minimum of 24 hours.

RESULTS

Glyphosate is a non-selective, post-emergent herbicide. Commercial formulations are predominantly aqueous solutions or concentrates of its isopropylamine salt. Instead of isopropylamine, which is a liquid, a salt available in solid form, sodium bicarbonate, was mixed with the technical acid. A mixture of the two components at a 1:1 weight ratio was dissolved in water, yielding a solution with a pH of 6.5. Subsequently, this ratio was used in granule formulations. An additional benefit from using $NaHCO_3$ arises from the evolution of $CO_2$ upon dissolution. The effervescent gas aids disintegration of the granule during its expansion to form bubbles, which enhances the rate of dissolution.

The results obtained for samples of glyphosate processed with Agrimax™ 3 adjuvant are summarized in Table 1. The amount of adjuvant required ranged from 15% to 20% (wt mix basis). The granules had good dissolution properties. Granule hardness and friability were significantly improved with the addition of 5% water, either premixed with Agrimax™ or introduced separately. The resulting granules were sufficiently hard and did not exhibit tackiness. The high water solubility of the solids allowed for dissolution during mixing. Liquid bridges which formed solidified upon drying to give strong bonds between the particles.

TABLE 1

Properties of Glyphosphate/Agrimax 3 Granules

| % Agrimax 3 | % Water Added | Dissolution, # Inversions | Friability Index | Crush Strength, g |
|---|---|---|---|---|
| 20 | 0 | 50 | 75 | 4 |
| 20 | 0 | 40 | 65 | 6 |
| 15 | 0 | 50 | 48 | 11 |
| 15 | 5 | 60 | 75 | 15 |
| 15 | 5 | 50 | 77 | 23 |
| 15 | 5 | 50 | 89 | 26 |

Various defoamers were added to the formulations during wet mixing to assess their effectiveness with respect to foam. A soda soap was found to provide adequate foam control at a 1% level.

A formulation consisting of 15% Agrimax™ 3 adjuvant with 1% defoamer, Roundup®, was selected for biological tests versus a fully formulated commercial product.

Biological Evaluation—Greenhouse tests of the experimental and commercial glyphosate formulations were run with three plant species—velvetleaf, foxtail and pigweed. Application rates chosen were 0.22 kg/ha, 0.56 kg/ha, and 1.12 kg/ha based on the equivalent acid form of glyphosate. In addition, ethoxylated tallow amine wetting agent (Ethomeen® T/25) was added to the experimental granule spray solution at the level of ½ part per part of acid equivalent. A similar type and level of wetting agent is present in the commercial formulation.

Phytotoxicity data was obtained for the glyphosate formulations on pigweed at application rates of 0.56 and 1.12 kg/ha, respectively. Plant damage was near 100% one week after treatment for both formulations. For all observation periods, there was no significant difference in phytotoxicity between the test formulation and Roundup®. A similar trend was observed for phytotoxicity against foxtail. Test results also were obtained with velvetleaf. At the lower application rate of 0.56 kg/ha, neither formulation was effective against the species. A statistically significant difference was obtained only at 1.12 kg/ha after 14 days, where Roundup® provided about 50% control. Measurements of the dry weights of plants at the conclusion of the test period were consistent with the phytotoxicity data. Both formulations showed equivalent efficacy against pigweed and foxtail.

The results herein demonstrate a substantial equivalency in efficacy and toxicity with Roundup®. Furthermore, the granules of the invention have the particular advantage of a solid formulation.

2,4-Dichlorophenoxyacetic acid 2,4-dichlorophenoxyacetic acid is a selective broadleaf herbicide used in large volume in amine salt form. As with glyphosate, sodium bicarbonate was combined with 2,4-dichlorophenoxyacetic acid to facilitate the formulation of granules. Due to the lower solubility of 2,4-D sodium salt compared to amine salt, the concentration of 2,4-D in the granules was reduced. Table 2 summarizes the results obtained for several compositions tested. At a 1:1 weight ratio of the solids, 2,4-D did not completely dissolve at 1% concentration. A greater excess of $NaHCO_3$, 5:8 weight ratio, was required for complete dissolution of 2,4-D. The resulting granules had good cohesiveness and did not require additional water for strength.

TABLE 2

Properties of 2,4-Dichlorophenoxyacetic Acid/Agrimax ™ 3 Granules

| 2,4-D (%) | $NaHCO_3$ (%) | Agrimax 3 (%) | Dissolution, # Inversions | Friability Index |
|---|---|---|---|---|
| 43 | 43 | 14 | >150 | 95 |
| 33 | 53 | 14 | 100 | 96 |
| 33 | 53 | 14 | 100 | 94 |

Chlorothalonil

Chlorothalonil is a widely used water insoluble fungicide commercially available only as wettable powders or water dispersible granules. A water dispersible granule as above was formulated with Agrimax™ 3 as the granulating fluid. A wet mix composition including 16.5% to 18% Agrimax 3 produced granules of very good quality. The Friability Index was above 95, and 85% was suspended, as determined by the filtration suspension test. The Sedimentation Index, as determined by the cone dispersion test, was below 1 (0.1 mL sediment/15 g granules).

What is claimed is:

1. A free-flowing granule made by drying a wet paste composition for forming free-flowing granules of an agriculturally active chemical, which can be dispersed or dissolved rapidly in water, and thereafter applied to a plant surface, comprises, by weight:

(a) 20–80% of an agriculturally active chemical,
   (b) 1–4% of a water-insoluble, film-forming polymer selected from a copolymer of 50% N-vinylpyrrolidone and 50% of a $C_{16}$ α-olefin or a copolymer of 20% N-vinylpyrrolidone and 80% of a $C_{20}$ α-olefin, which adheres to the plant surface and resists wash-off of the agricultural chemical by rain water thus extending the contact time of the chemical thereon,
   (c) 0.5–3% of an anionic surfactant,
   (d) 2–10% of a $C_6$–$C_{24}$ alkylpyrrolidone,
   (e) 2–8% of water, and, optionally,
   (f) 0–4% of a $C_1$–$C_4$ alkylpyrrolidone,
   (g) 0–80% of a salt former,
   (h) 0–4% of a disintegrant,
   (i) 0–10% of a dispersant,
   (j) 0–8% of a wetting agent, and
   (k) 0–2% of a defoamer.

2. A granule of claim 1 made by drying a wet paste composition of claim 1 wherein (a) is 50–70%; (b) 1.5–2.5%; (c) 1–2%; (d) 5–7.5%; (e) 3–6%; (f) 0–3%; (g) 0–50%; (h) 0–3%; (i) 0–8%; (j) 0–5% and (k) 0–1%.

3. A free-flowing granule of claim 1 wherein (e), the water component, is absent.

4. A free-flowing granule of claim 2 wherein (e), the water component, is absent.

* * * * *